United States Patent [19]

Hyodo

[11] Patent Number: 5,781,455
[45] Date of Patent: Jul. 14, 1998

[54] ARTICLE OF MANUFACTURE COMPRISING COMPUTER USABLE MEDIUM FOR A PORTABLE BLOOD SUGAR VALUE MEASURING APPARATUS

[75] Inventor: Hiroshi Hyodo, Kyoto, Japan

[73] Assignee: Kyoto Daiichi Kagaku Co., Ltd., Kyoto-fu, Japan

[21] Appl. No.: 696,742

[22] Filed: Aug. 14, 1996

Related U.S. Application Data

[63] Continuation-in-part of Ser. No. 331,813, Oct. 31, 1994, Pat. No. 5,589,045.

[30] Foreign Application Priority Data

Nov. 2, 1993 [JP] Japan ................... 5-274228

[51] Int. Cl.$^6$ .................................. G05B 23/02
[52] U.S. Cl. ........................... 364/579; 204/403
[58] Field of Search ........................ 364/579, 580; 204/406, 403, 407, 401; 435/817

[56] References Cited

U.S. PATENT DOCUMENTS 5,266,179  11/1993  Nankai et al. .
5,352,351  10/1994  White et al. .
5,589,045  12/1996  Hyodo .................... 204/406

FOREIGN PATENT DOCUMENTS 0 245073  11/1987  European Pat. Off. .
0 645626   3/1995  European Pat. Off. .
94/29705  12/1994  WIPO .

*Primary Examiner*—James P. Trammell
*Attorney, Agent, or Firm*—Birch, Stewart, Kolasch & Birch, LLP

[57] ABSTRACT

An article of manufacture includes a computer usable medium, including computer-readable program code instructions embodied therein, for causing a computer to manage data in a measuring apparatus. The instructions include a detecting portion utilized for causing the computer to detect whether an electrode has been mounted on the measuring apparatus. A characteristic measuring portion is utilized for causing the computer to measure a characteristic of the electrode to determine what type of electrode has been mounted on the measuring apparatus. A clocking portion is utilized for causing the computer to clock a first period of time after the computer has measured the characteristic of the electrode. A determining portion is utilized for causing the computer to determine whether to measure density of an element included in a biological body fluid or whether to read out measured density data. A density measuring portion is utilized for causing the computer to measure density of the element included in the biological body fluid which has been placed on the electrode. A density storing portion is utilized for causing the computer to store a measured density of the element included in the biological body fluid in a storing device. A read out portion is utilized for causing the computer to read out measured density data stored in the storing device.

15 Claims, 12 Drawing Sheets

Fig.6

① [A] → "A" IS DISPLAYED FOR 1 SECOND → [▢▢▢] AVERAGE VALUE IS DISPLAYED FOR 2 SECONDS

② [3] → "3" IS DISPLAYED FOR 1 SECOND → [▢▢▢] STORED DATA OF MEMORY NO.3 (LATEST DATA) IS DISPLAYED FOR 2 SECONDS

③ [2] → "2" IS DISPLAYED FOR 1 SECOND → [▢▢▢] STORED DATA OF MEMORY NO.2 IS DISPLAYED FOR 2 SECONDS

..........

⑩ [5] → "5" IS DISPLAYED FOR 1 SECOND → [▢▢▢] STORED DATA OF MEMORY NO.5 IS DISPLAYED FOR 2 SECONDS

⑪ [4] → "4" IS DISPLAYED FOR 1 SECOND → [▢▢▢] STORED DATA OF MEMORY NO.4 (OLDEST DATA) IS DISPLAYED FOR 2 SECONDS

⑫ AUTOMATICALLY OFF

ARTICLE OF MANUFACTURE COMPRISING COMPUTER USABLE MEDIUM FOR A PORTABLE BLOOD SUGAR VALUE MEASURING APPARATUS

CROSS-REFERENCE TO RELATED APPLICATIONS

This is a Continuation-In-Part of application Ser. No. 08/331,813, filed on Oct. 31, 1994, U.S. Pat. No. 5,587,045.

BACKGROUND OF THE INVENTION

1. Field of the Invention

The present invention relates to an article of manufacture comprising a computer usable medium, including computer-readable program code means embodied therein, for causing a computer to manage data in a measuring apparatus. Particularly, the measuring apparatus can be used by a patient himself/herself to measure his/her blood sugar value.

2. Conventional Art

A portable blood sugar value-measuring apparatus is known which stores data of blood sugar values sequentially measured by a diabetic for himself/herself. In reading out a plurality of the stored data of the measured blood sugar values in such a conventional blood sugar value-measuring apparatus, an operation button provided on the surface thereof is depressed to display them sequentially on a display portion.

As disclosed in Japanese Laid-Open Patent Publication No. 357452/1992, the present applicant proposed a blood sugar value-measuring apparatus having no operation buttons provided thereon. In the blood sugar value-measuring apparatus disclosed in the Patent Publication, various types of electrodes, such as a blood sugar value-measuring one, a correcting one, and the like, each having its own resistance value, are installed on the blood sugar value-measuring apparatus. When one of them is mounted on the blood sugar value-measuring apparatus, its resistance value is detected and then, the blood sugar value-measuring apparatus is set to an operation state. In addition, the type of electrode which has been installed on the blood sugar value-measuring apparatus can be detected based on its resistance value. In this manner, a function of each type of electrode is performed in the blood sugar value-measuring apparatus. This construction eliminates the need for the provision of an operation switch.

SUMMARY OF THE INVENTION

An object of the present invention is to provide an article of manufacture comprising a computer usable medium, including computer-readable program code means embodied therein, for causing a computer to manage data in a measuring apparatus having no operation buttons in order to eliminate the provision of the operation on reading a plurality of measured values with respect to biological body fluid, storing the measured values in a storing means sequentially, and reading the measured values from the storing means, or the like.

In accomplishing the aforementioned object, according to one aspect of the present invention of the article of manufacture comprising a computer usable medium, there is provided a computer usable medium, including computer-readable program code means embodied therein, for causing a computer to manage data in a measuring apparatus, the computer-readable program code means in the article of manufacture comprising:

computer-readable program code detecting means for causing the computer to detect whether an electrode has been mounted on the measuring apparatus;

computer-readable program code characteristic measuring means for causing the computer to measure a characteristic of the electrode to determine what type of electrode has been mounted on the measuring apparatus;

computer-readable program code clocking means for causing the computer to clock a first period of time after the computer has measured the characteristic of the electrode;

computer-readable program code determining means for causing the computer to determine whether to measure density of an element included in a biological body fluid or whether to read out measured density data;

computer-readable program code density measuring means for causing the computer to measure density of the element included in the biological body fluid which has been placed on the electrode;

computer-readable program code density storing means for causing the computer to store a measured density of the element included in the biological body fluid in a storing means;

computer-readable program code read out means for causing the computer to read out measured density data stored in the storing means; and computer-readable program code output means for causing the computer to output the measured density data read out from the storing means.

The article of manufacture may further comprise computer-readable program code erasing means for causing the computer to determine whether to erase the measured density data in the storing means.

The article of manufacture may further comprise computer-readable program code writing permission/nonpermission determining means for causing the computer to determine whether to store the measured density data to the storing means.

The article of manufacture may further comprise computer-readable program code value displaying means for causing the computer to display a value based on a resistance value of an electrode mounted on the measuring apparatus when the type of electrode mounted on the measuring apparatus is a type for measuring the resistance value.

BRIEF DESCRIPTION OF THE DRAWINGS

These and other objects and features of the present invention will become clear from the following description taken in conjunction with the preferred embodiments thereof with reference to the accompanying drawings throughout in which like parts are designated by like reference numerals, and in which:

FIG. 6 is a view showing the display method of data of a blood sugar value stored in a RAM;

DETAILED DESCRIPTION OF THE PREFERRED EMBODIMENTS

Figure 1:
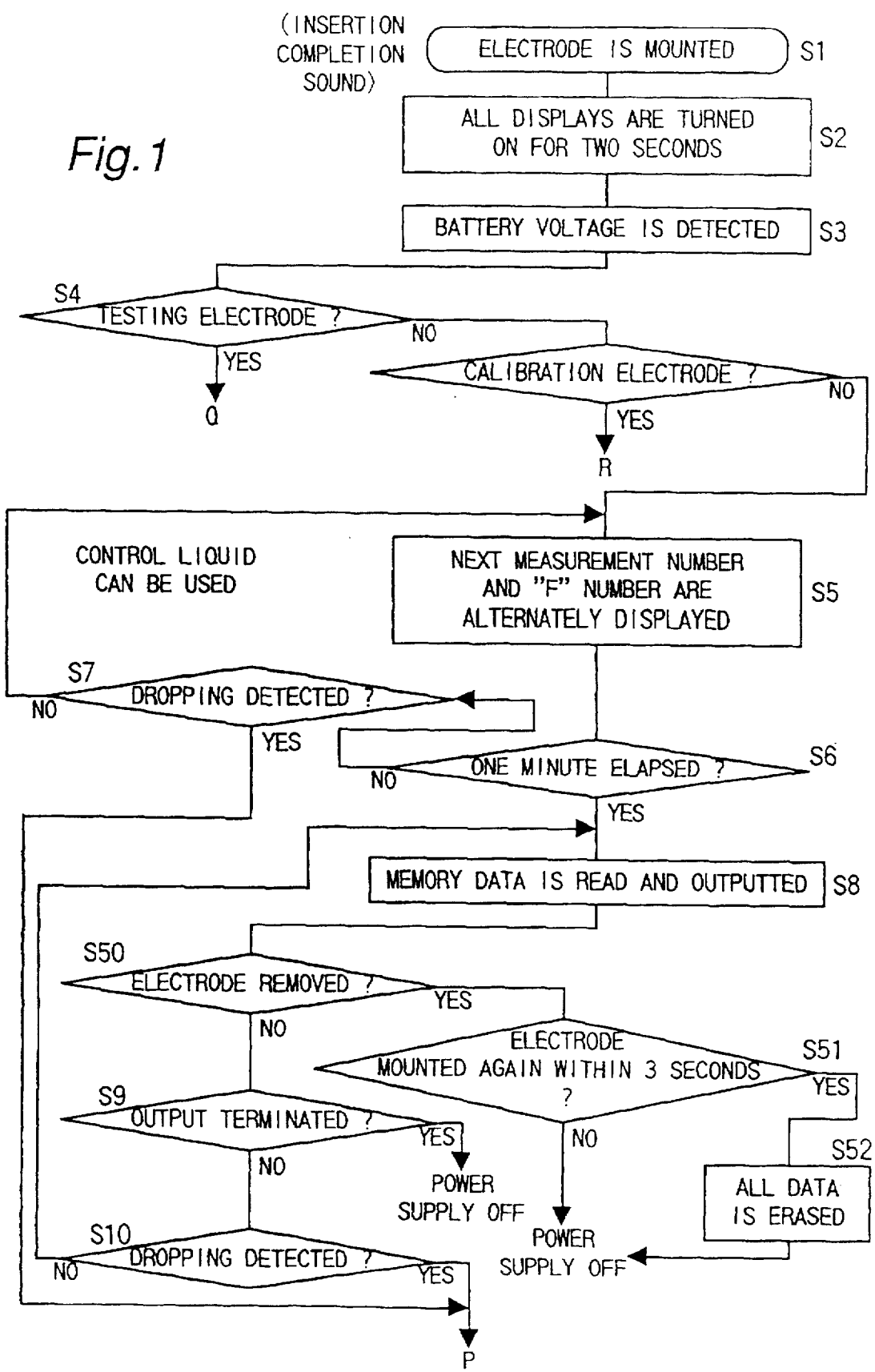
FIG. 1 is a flowchart showing the operation of a data managing method read from computer-readable program code means embodied in a computer usable medium in an article of manufacture according to an embodiment of the present invention.

Before the description of the present invention proceeds, it is to be noted that like parts are designated by like reference numerals throughout the accompanying drawings.

In the embodiment, an article of manufacture comprising a computer usable medium is used in a portable measuring apparatus. The computer usable medium includes computer-readable program code means embodied therein and causes the computer to manage data in the portable measuring apparatus.

The portable measuring apparatus of the embodiment is used to measure density of an element included in biological body fluid such as total blood, blood plasma, blood serum, urine, and so on. As the element, Glucose, lactic acid, cholesterol, uric acid, triglyceride, and so on are included.

The portable measuring apparatus does not have an operation switch, similarly to the blood sugar value-measuring apparatus disclosed in the Patent Publication previously described. The operation switch means a switch which is mounted on an outer surface of the measuring apparatus and can be manually operated by a user. An example of the outline of the construction of the measuring apparatus is described below.

Figure 7:
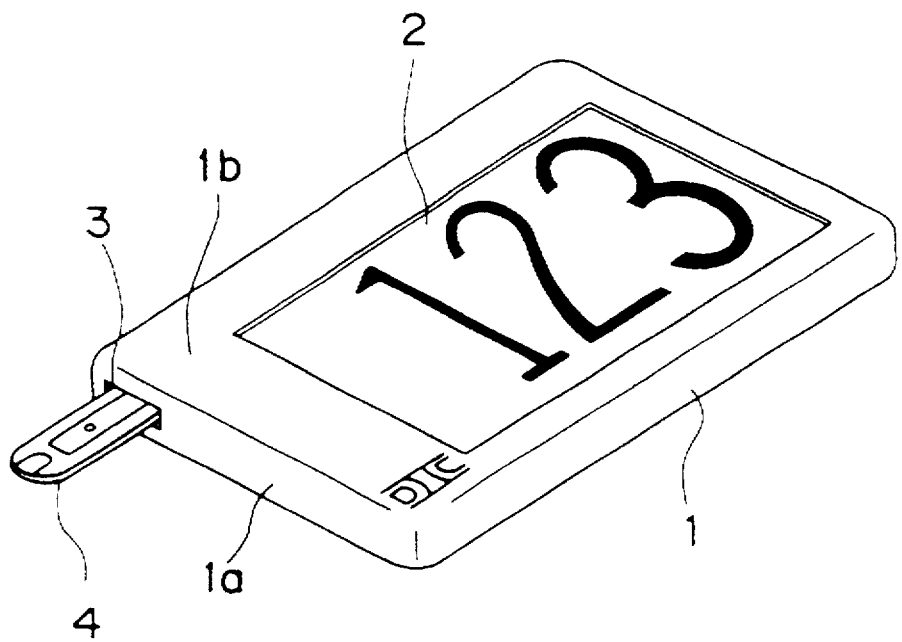
FIG. 7 is a perspective view of an example of a blood sugar value-measuring apparatus to which the data managing method is applied.
Figure 10:
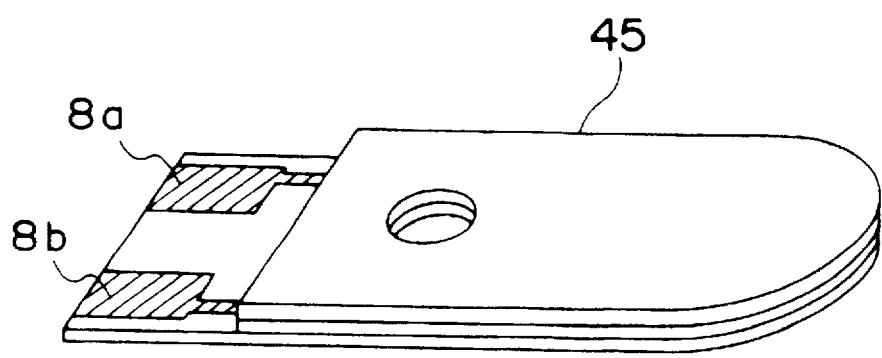
FIG. 10 is a perspective view showing the electrode shown in FIG. 7.

Referring to FIG. 7, the measuring apparatus 1 is rectangular and plate-shaped. There is formed on a side surface 1a of the measuring apparatus 1 in the thickness direction thereof a connector 3 into which various electrodes 45 such as a measuring electrode 4 for measuring density of the element included in the biological body fluid, e.g., blood sugar value as shown in FIG. 10 are inserted. A liquid crystal display (LCD) 2 occupying a large area of the upper surface 1b of the measuring apparatus 1 is formed thereon.

Figure 8:
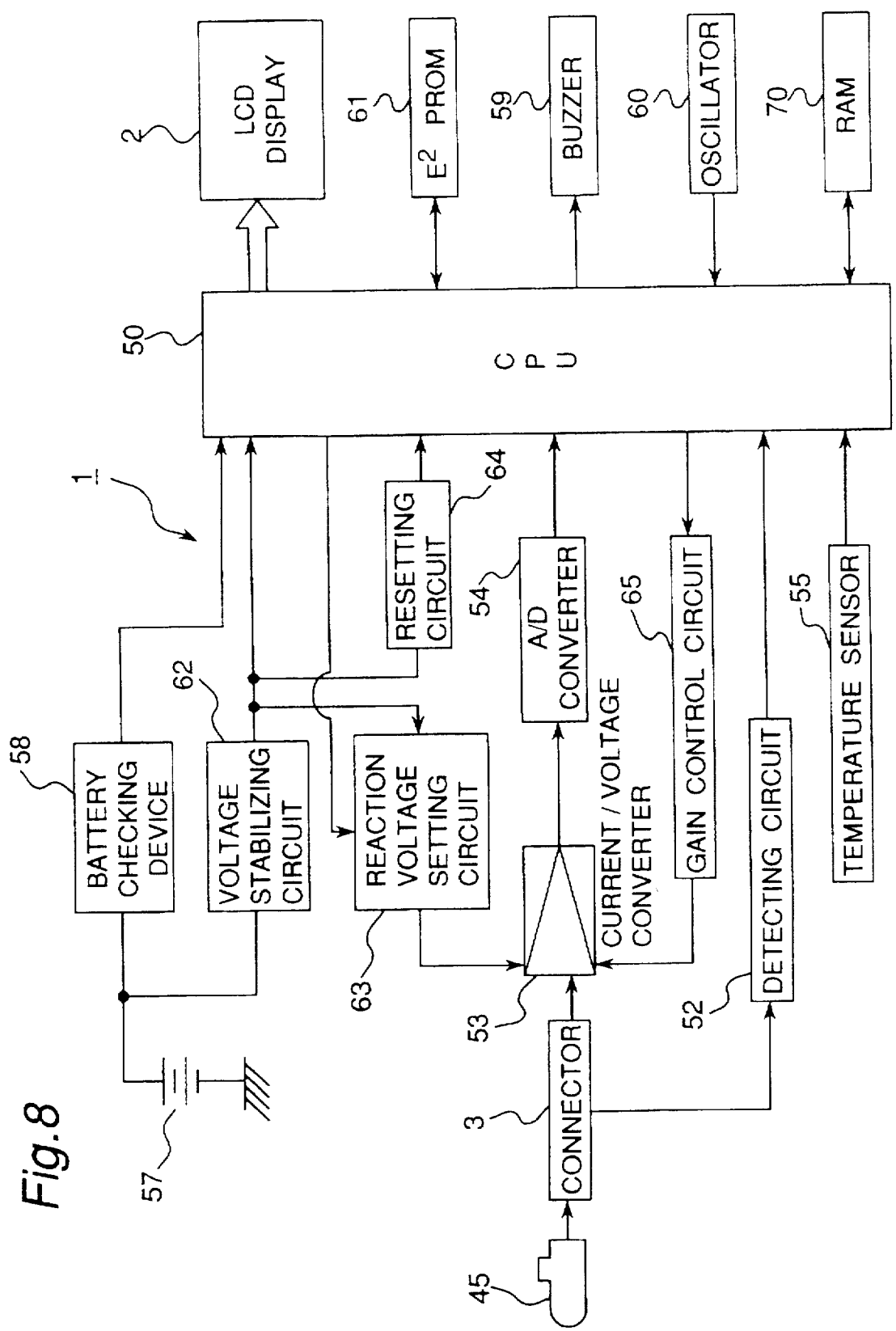
FIG. 8 is a block diagram showing an embodiment of the construction of the blood sugar value-measuring apparatus shown in FIG. 7.

The circuit construction of the measuring apparatus 1 is described below with reference to FIG. 8.

A power battery 57 incorporated in the measuring apparatus 1 is connected with a battery checking device 58 which decides whether the voltage of the power battery 57 is in a predetermined range. The output side of the battery checking device 58 is connected with a CPU 50. The power battery 57 is connected with the CPU 50 via a voltage stabilizing circuit 62, thus supplying the CPU 50 with a predetermined electric power.

The connector 3 is connected with the input side of a detecting circuit 52 which detects whether or not the electrode 45 has been mounted on the connector 3, thus outputting a signal indicating that the electrode 45 has been mounted on the connector 3 if the electrode 45 has been mounted thereon. The connector 3 is also connected with the input side of a current/voltage converter 53 for converting electric current flowing through the electrode 45 connected with the connector 3 into a voltage. The output side of the detecting circuit 52 is connected with the CPU 50 so that the detecting circuit 52 outputs a signal indicating that the electrode 45 has been mounted on the connector 3 to the CPU 50. The current/voltage converter 53 is connected with the output side of a reaction voltage setting circuit 63 connected with the output side of the voltage stabilizing circuit 62. The reaction voltage setting circuit 63 supplies a predetermined reaction voltage to the electrode 45 mounted on the connector 3 via the current/voltage converter 53, when the reaction voltage setting circuit 63 has been supplied with a control signal outputted from the CPU. 50 upon receipt of a signal from the detecting circuit 52. The current/voltage converter 53 is connected with the output side of a gain control circuit 65, the input side of which is connected with the CPU 50. The output side of the current/voltage converter 53 is connected with the CPU 50 via an A/D converter 54. Thus, the intensity of electric current flowing through the electrode 45 is converted into a digital value and the digital value is supplied to the CPU 50 as data.

The CPU 50 is connected with a RAM (random access memory) 70 for storing the data of density value of the element included in the biological body fluid measured by the measuring electrode 4. The RAM 70 can store the data of latest 10 measured density values and the data of measured values of control liquid which will be described later.

The CPU 50 is also connected with the output side of a resetting circuit 64, the input side of which is connected with the output side of the voltage stabilizing circuit 62; the output side of a temperature sensor 55; the output side of an oscillator 60 for outputting clock signals; the input side of the LCD 2; the input side of a buzzer 59 for generating an alarm; and the input and output sides of a semiconductor memory 61 for storing the correction value for each measuring apparatus.

Also, the semiconductor memory 61 includes computer-readable program code means read out by the CPU 50 for managing data in operations as described below of the measuring apparatus. The main program code means included in the semiconductor memory 61 comprises computer-readable program code detecting means for causing the computer to detect whether an electrode has been mounted on the measuring apparatus;

computer-readable program code characteristic measuring means for causing the computer to measure a characteristic of the electrode to determine what type of electrode has been mounted on the measuring apparatus;

computer-readable program code clocking means for causing the computer to clock a first period of time after the computer has measured the characteristic of the electrode;

computer-readable program code determining means for causing the computer to determine whether to measure density of an element included in a biological body fluid or whether to read out measured density data;

computer-readable program code density measuring means for causing the computer to measure density of the element included in the biological body fluid which has been placed on the electrode;

computer-readable program code density storing means for causing the computer to store a measured density of the element included in the biological body fluid in a storing means;

computer-readable program code read out means for causing the computer to read out measured density data stored in the storing means; and computer-readable program code output means for causing the computer to output the measured density data read out from the storing means.

Also, the program code means may further comprise computer-readable program code erasing means for causing the computer to determine whether to erase the measured density data in the storing means.

Also, the program code means may further comprise computer-readable program code writing means for causing the computer to determine whether to store the measured density data to the storing means.

Also, the program code means may further comprise computer-readable program code value displaying means for causing the computer to display a value based on a resistance value of an electrode mounted on the measuring apparatus when the type of electrode mounted on the measuring apparatus is a type for measuring the resistance value.

The portable measuring apparatus of the embodiment measures density of glucose and then displays a blood sugar value based on the measured density of glucose. Accordingly, the semiconductor memory 61 in the portable measuring apparatus of the embodiment includes computer-readable program code means with respect to managing the blood sugar value data.

Each of the portable measuring apparatuses has each semiconductor memory respectively including computer-readable program code means with respect to managing the data of the to-be-measured element.

The outline of the fundamental operation, similar to that disclosed in the above-described Patent Publication, of the measuring apparatus 1 having the above construction is described below.

The main component contained in the reagent layer of the measuring electrode 4 consists of oxidoreductase having a substrate contained in biological body fluid and a redox compound serving as a substance for transporting electrons of the oxidoreductase.

The measuring object measured by the measuring electrode 4 is biological body fluid such as total blood, blood plasma, blood serum, urine, and so on.

The measuring element of the biological body fluid is glucose, lactic acid, cholesterol, uric acid, triglyceride, and so on.

For example, when the substrate is glucose, the glucose oxidase (hereinafter referred to as GOD) is used as oxidoreductase and potassium ferricyanide serving as mediator. When the electrode is supplied with measured liquid containing glucose, the mediator, namely, potassium ferricyanide and glucose react with each other in the presence of GOD as shown by an equation 1 shown below to form potassium ferrocyanide corresponding to the density of glucose. At a certain interval, an electric circuit is used in this embodiment to apply a certain voltage to both ends of a lead of the electrode. The intensity of oxidation current thus obtained is proportional to the density of potassium ferrocyanide formed by the reaction shown by the equation 1, namely, the density of glucose. Thus, the density of glucose contained in the measured liquid can be measured by measuring the intensity of electric current generated by the application of the voltage to the electrode.

[Equation 1]

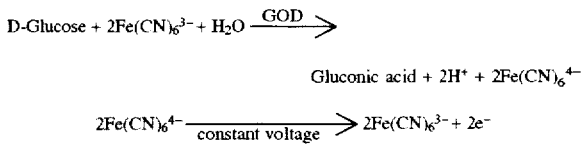

For example, when the substrate is lactic acid, the lactate oxidase (hereinafter referred to as LOD) is used as oxidoreductase and potassium ferricyanide serving as mediator. When the electrode is supplied with measured liquid containing lactic acid, the mediator, namely, potassium ferricyanide and lactic acid react with each other in the presence of LOD as shown by an equation 2 shown below to form potassium ferrocyanide corresponding to the density of lactic acid. At a certain interval, an electric circuit is used in this embodiment to apply a certain voltage to both ends of a lead of the electrode. The intensity of oxidation current thus obtained is proportional to the density of potassium ferrocyanide formed by the reaction shown by the equation 2, namely, the density of lactic acid. Thus, the density of lactic acid contained in the measured liquid can be measured by measuring the intensity of electric current generated by the application of the voltage to the electrode.

[Equation 2]

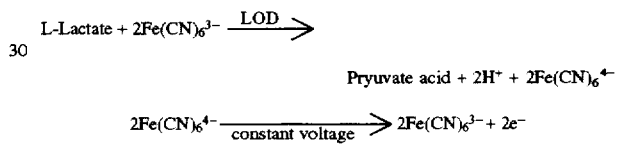

For example, when the substrate is cholesterol, the cholesterol oxidase (hereinafter referred to as ChOD) is used as oxidoreductase and potassium ferricyanide serving as mediator. When the electrode is supplied with measured liquid containing cholesterol, the mediator, namely, potassium ferricyanide and cholesterol react with each other in the presence of ChOD as shown by an equation 3 shown below to form potassium ferrocyanide corresponding to the density of cholesterol. At a certain interval, an electric circuit is used in this embodiment to apply a certain voltage to both ends of a lead of the electrode. The intensity of oxidation current thus obtained is proportional to the density of potassium ferrocyanide formed by the reaction shown by the equation 3, namely, the density of cholesterol. Thus, the density of cholesterol contained in the measured liquid can be measured by measuring the intensity of electric current generated by the application of the voltage to the electrode.

[Equation 3]

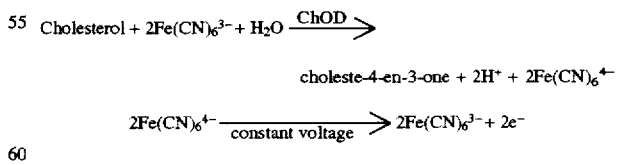

In a following explanation, it is taken as an example that the blood is selected from among the biological body fluid and then the blood sugar value is measured by the measuring apparatus.

First, the measuring electrode 4 is inserted into the connector 3. When the detecting circuit 52 has detected the insertion of the measuring electrode 4 into the connector 3, the reaction voltage setting circuit 63 serving as the power supply applies a predetermined voltage necessary for obtaining response electric current to the terminal of the connector 3. Thus, the response electric current flowing through the measuring electrode 4 inserted into the connector 3 is converted into a voltage by the current/voltage converter 53 and then, the voltage is converted into binary data by the A/D converter 54.

The CPU 50 reads an output signal of the A/D converter 54, thus executing processing. The measuring electrode 4 containing enzyme is considered to be a kind of a resistor. Supposing that the resistance value of the measuring electrode 4 is Rs; the amplification resistance of the current/voltage converter 53 is Rf; and a voltage to be applied to the terminal of the connector 3 is E, the output voltage $E_0$ of the current/voltage converter 53 is found by the following equation:

$$E_0 = E + i \times Rf = E + (E/Rs) \times Rf$$

The resistance value Rs of the measuring electrode 4 is as great as an infinite quantity when the measuring electrode 4 is not supplied with to-be-measured liquid. Accordingly, the intensity (i) of electric current is very small and thus, the output voltage $E_0$ of the current/voltage converter 53 is nearly equal to E.

When the measuring electrode 4 is supplied with the to-be-measured liquid, the resistance value Rs of the measuring electrode 4 drops rapidly. Consequently, the output voltage $E_0$ increases rapidly. Therefore, the dropping of the liquid to the measuring electrode 4 can be detected by always monitoring the output voltage $E_0$ of the current/voltage converter 53.

Thus, the CPU 50 detects the change in the output voltage $E_0$ of the current/voltage converter 53 based on a signal supplied thereto from the A/D converter 54, thus starting a measuring timer automatically.

In adjusting the measuring apparatus 1, an adjusting electrode is used. The adjusting electrode has a configuration similar to that of the measuring electrode 4 and a constant resistance value much smaller than that (infinite quantity) of an unused electrode. That is, when the voltage of the adjusting electrode is measured, the adjusting electrode indicates a stable and constant voltage from the beginning of measurement. Thus, the CPU 50 can discriminate several kinds of adjusting electrodes from each other based on different voltages.

The term adjusting electrode is used generically to describe several types of electrodes including an adjusting mode switch-over electrode, an electrode for correcting error between the apparatuses, a calibrating electrode, a testing electrode, a unit-switching electrode, and the like. If the adjusting electrode is determined to be the calibrating electrode, the CPU 50 automatically discriminates and selects a proper working curve corresponding to the calibrating electrode from a plurality of working curves stored in the measuring apparatus, according to the resistance value (voltage) thereof.

When the adjusting electrode is determined to be the testing electrode, the voltage thereof is converted into a density, and the density is displayed on the LCD 2. The CPU 50 decides whether or not the measuring apparatus is abnormal based on the density.

When the adjusting electrode is determined to be the unit-switching electrode, the voltage thereof is automatically altered/converted into each density unit (for example, mg/dl, mmol/L) so as to display the density unit on the LCD 2. Table 1 shows relations between the resistance value and the working curve for each calibrating electrode.

TABLE 1

| calibrating electrode No. | resistance value (KΩ) | working curve No. |
|---|---|---|
| 0 | 27 | F - 0 |
| 1 | 30 | F - 1 |
| 2 | 33 | F - 2 |
| 3 | 36 | F - 3 |
| 4 | 39 | F - 4 |
| 5 | 43 | F - 5 |
| 6 | 47 | F - 6 |
| 7 | 51 | F - 7 |
| 8 | 56 | F - 8 |
| 9 | 62 | F - 9 |

It is possible to increase the number of terminals of the connector 3 so as to insert the calibrating electrode or the testing electrode into the terminals other than the terminal into which the electrode is inserted.

There is a possibility that a method of discriminating the calibrating electrode or the testing electrode from other kinds of electrodes based on only the resistance value thereof leads to a decision that an electrode used which has been erroneously inserted into the connector 3 is the calibrating electrode or the testing electrode. In order to prevent such an erroneous decision, the following method is adopted in the portable measuring apparatus 1.

A voltage $E_{01}$ of an electrode inserted into the connector 3 is measured when the power supply is turned on, and a voltage $E_{02}$ thereof is measured again at an interval of several seconds in relation to the point when the power supply is turned on. The rate of change ($\Delta E$) in the two voltages is calculated. If the rate of change is greater than a predetermined level, it is decided that the electrode is the used one, and the result is displayed on the LCD 2. If the rate of change in the voltages is smaller than the predetermined level, it is decided that the electrode is the calibrating one or the testing one.

[Equation 4]

$$\Delta E = |(E_{01} - E_{02})/E_{01}|$$

Figure 11:
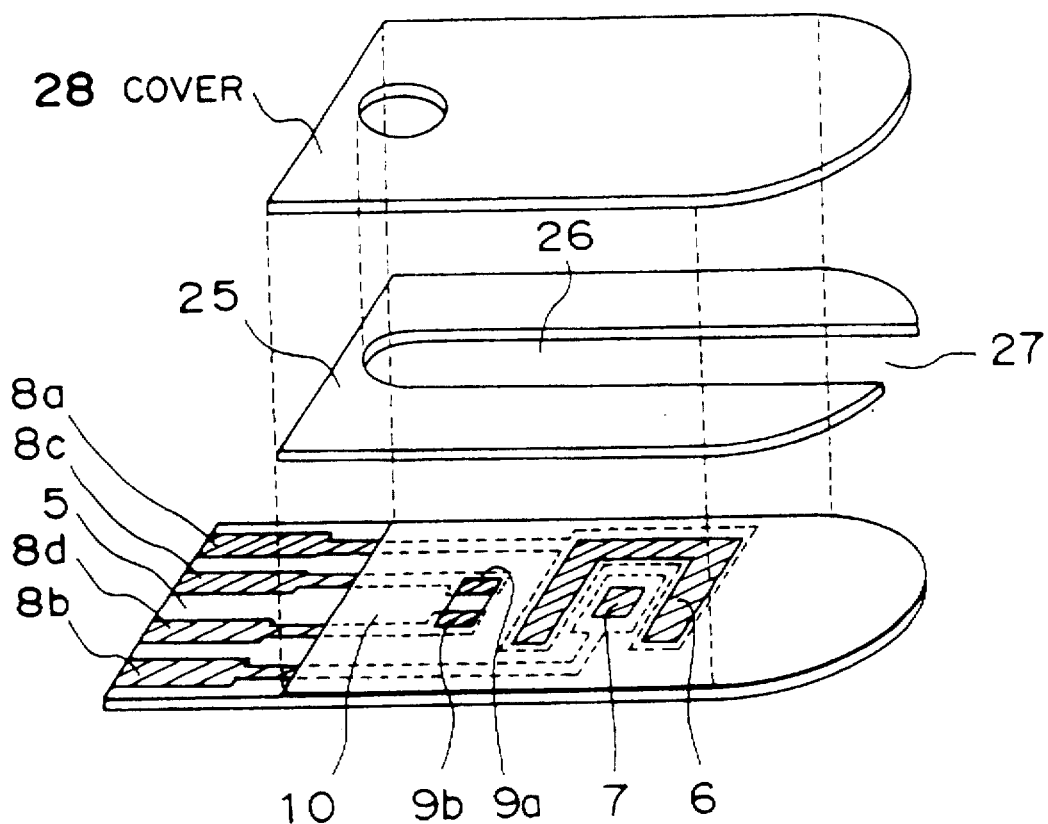
FIG. 11 is an exploded perspective view showing another electrode.

If an unused electrode behaves similarly to an electrode used because the former absorbs moisture at a high humidity, liquid junction detecting terminals 9a and 9b are disposed alongside the electrode as shown in FIG. 11. Supposing that the liquid junction detecting terminals 9a and 9b are provided, when the resistance value therebetween is infinite, it is decided by the CPU 50 that there is no liquid junctions and that the electrode inserted into the connector 3 is unused, whereas if the resistance value therebetween is low, it is decided that the electrode has been already used.

Figure 12:
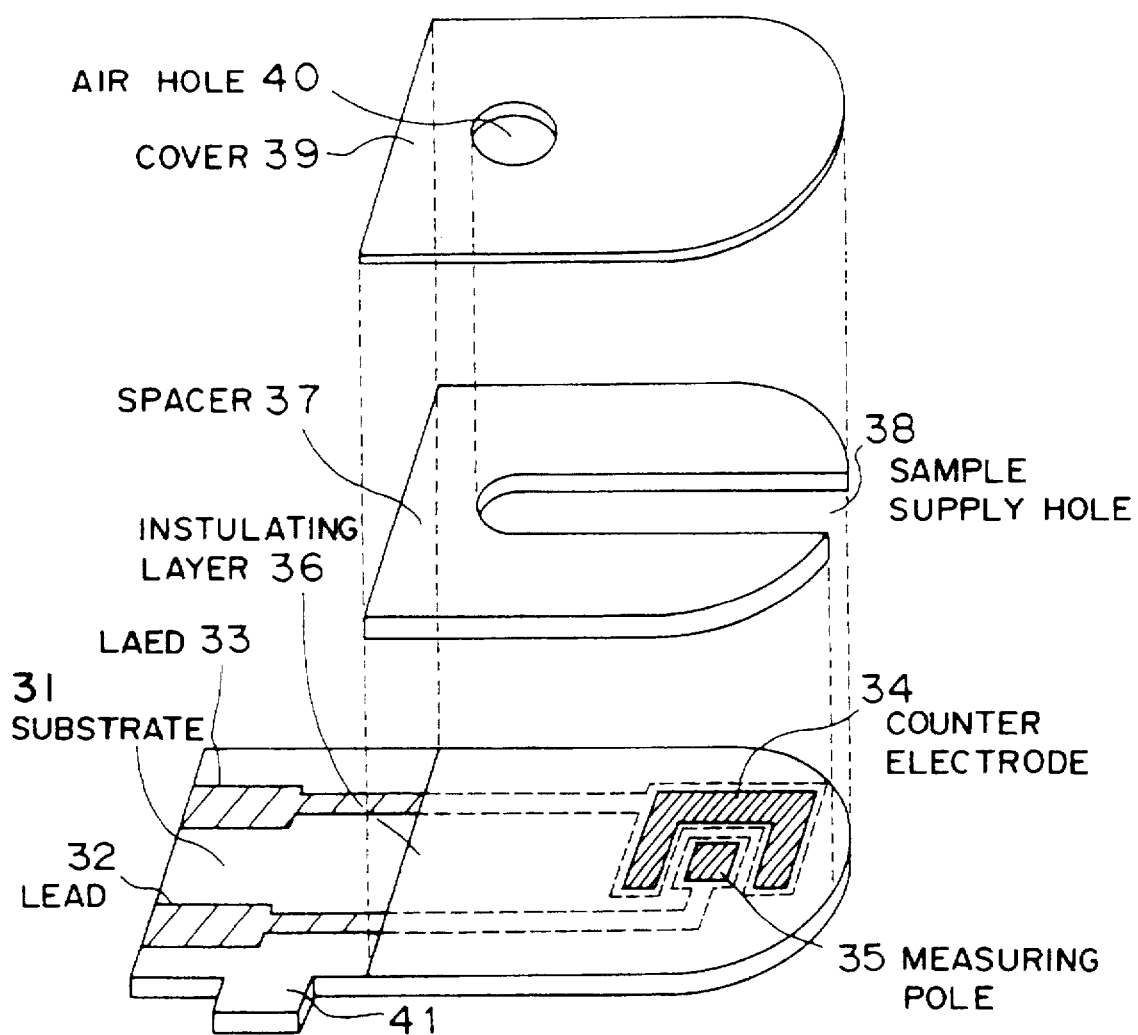
FIG. 12 is an exploded perspective view showing still another electrode.
Figure 13:
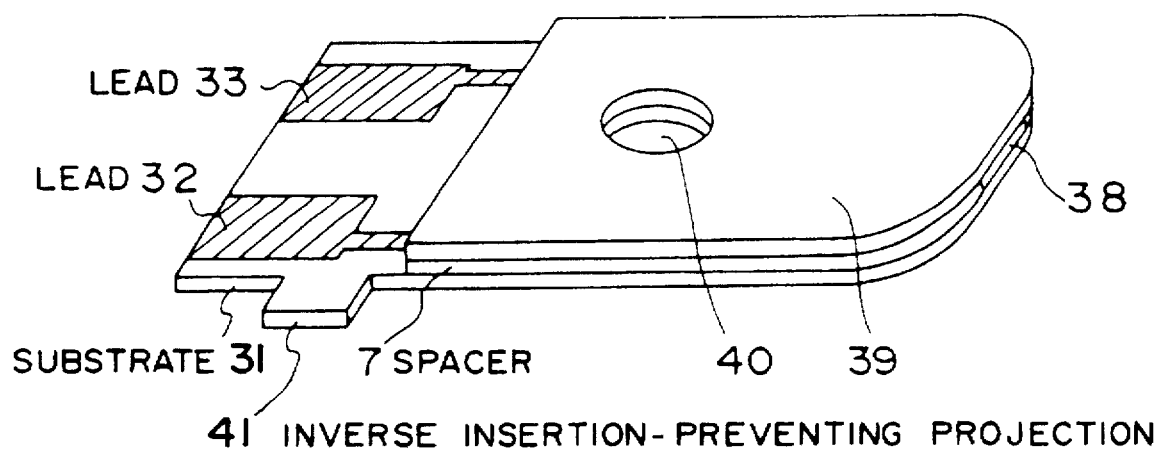
FIG. 13 is a perspective view showing the assembled electrode shown in FIG. 12.

FIG. 12 is a detailed exploded perspective view showing another embodiment of an electrode. FIG. 13 is a perspective view showing the assembled electrode.

There are provided on a substrate 31 a counter electrode 34, a measuring pole 35, leads 33, 32 connected with the counter electrode 34 and the measuring pole 35, respectively, and an insulating layer 36. Although not shown in FIG. 12, a reaction layer containing an enzyme and a mediator formed on the substrate 31 covers the counter electrode 34 and the measuring pole 35. A cover 39 is fixed to the upper surface of the substrate 31 via a spacer 37. To-be-measured liquid is introduced from a supply hole 38 to the counter electrode 34 and the measuring pole 35 by means of capillary action. Reference numeral 40 denotes an air introducing hole. An inverse insertion-preventing projection 41 projects from a side surface of the electrode 45. When the electrode 45 is inserted into the connector 3 normally, the projection 41 is inserted into the gap, whereas if the electrode 45 is inserted into the connector 3 upside down, the projection 41 prevents the electrode 45 from being inserted into the gap.

The operation of the blood sugar value-measuring apparatus disclosed in the above-described Patent Publication can be carried out by the measuring apparatus 1.

Furthermore, the measuring apparatus 1 according to this embodiment has each function of storing a measured blood sugar value, measuring the blood sugar value of the control liquid, reading the data of the measured blood sugar value stored in the RAM 70, and erasing the data of the measured blood sugar values. The CPU 50 executes the following various controls which will be described below.

An embodiment of the data managing method applied to the portable measuring apparatus 1 having the above-described construction and performing the above-described operation is described below.

Figure 2:
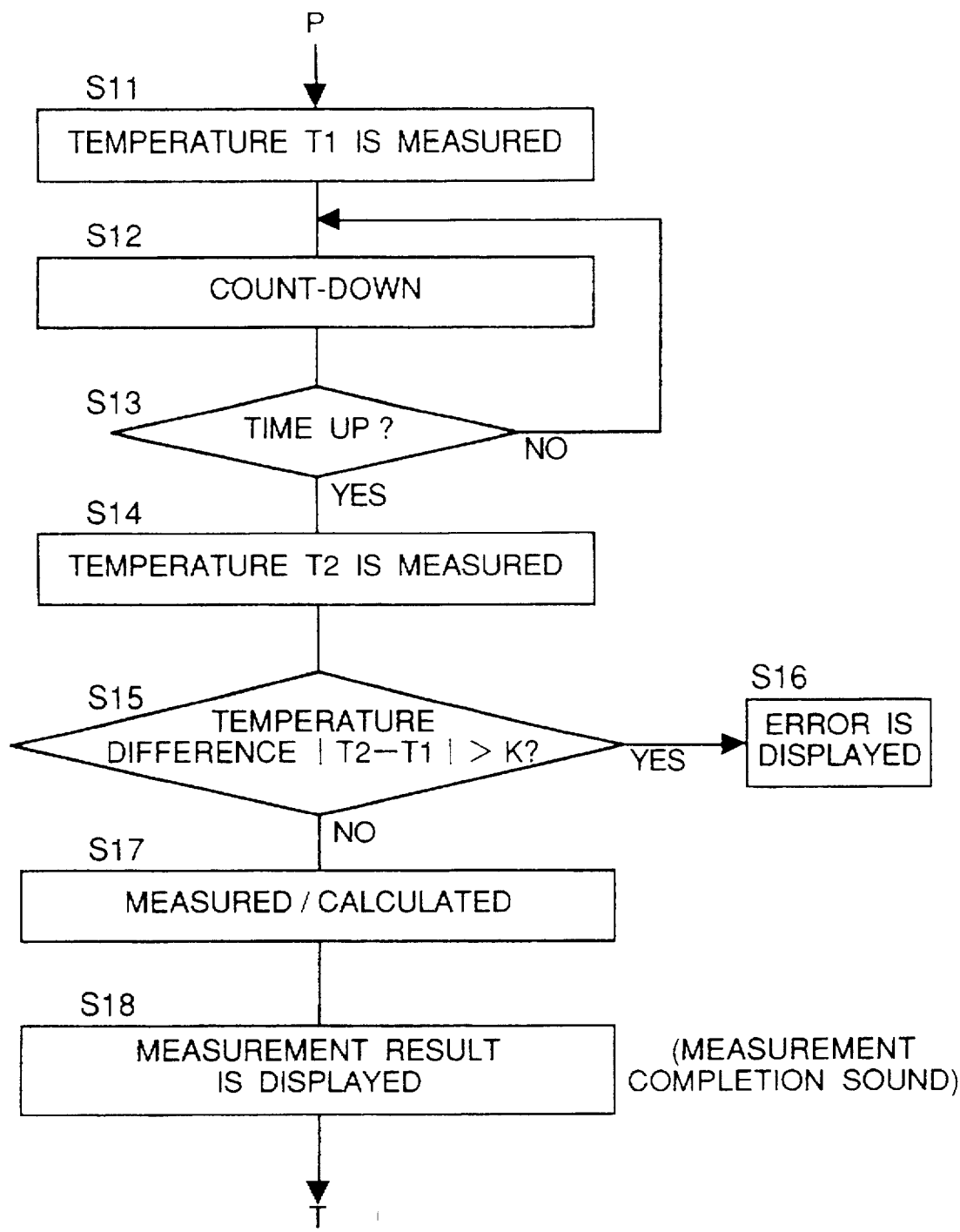
FIG. 2 is a flowchart subsequent to the flowchart shown in FIG. 1.
Figure 3:
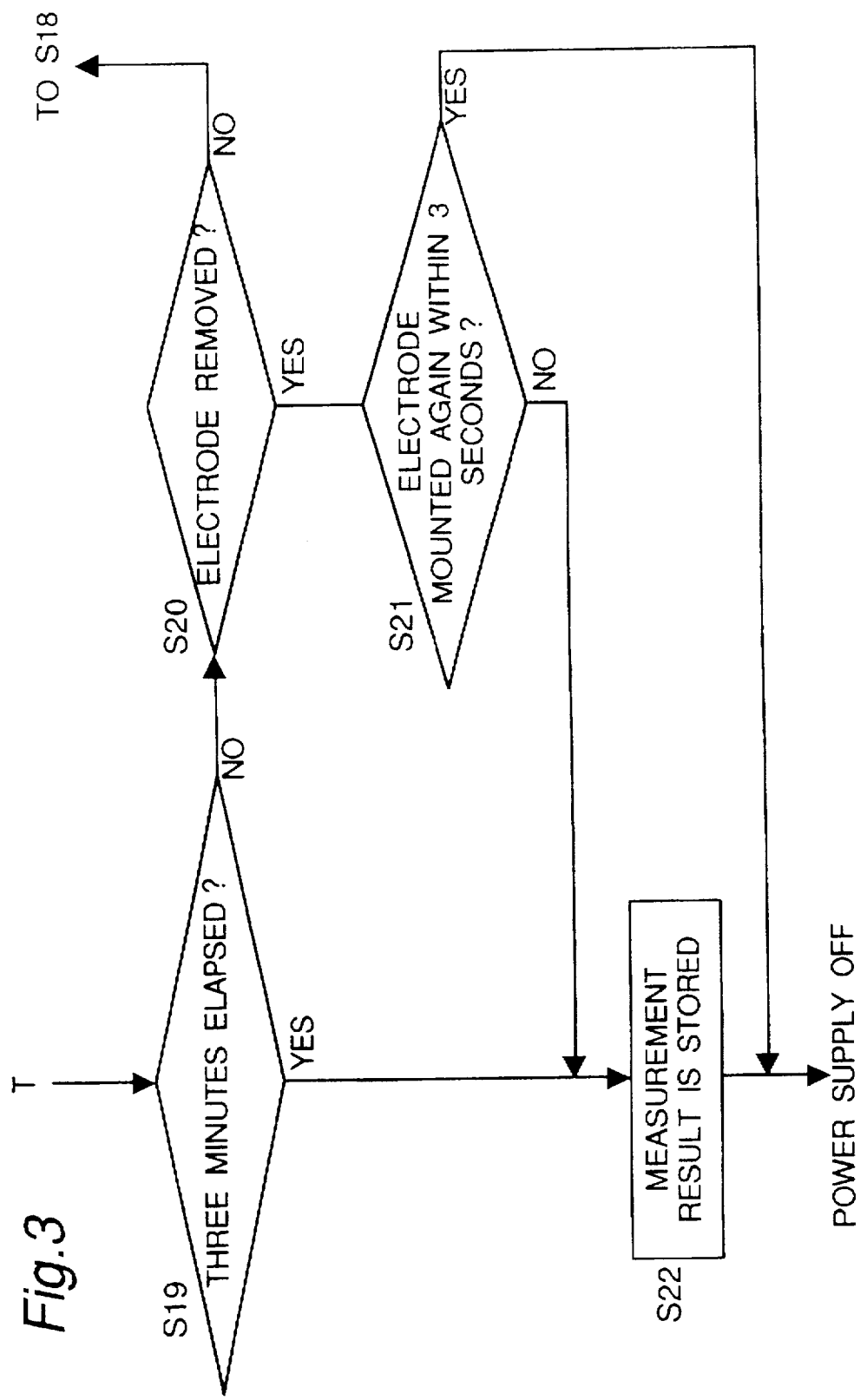
FIG. 3 is a flowchart subsequent to the flowchart shown in FIG. 2.

First, an embodiment of the data managing method to be carried out by the portable measuring apparatus 1 in performing a normal blood sugar value-measuring function is described below with reference to FIGS. 1, 2, and 3. FIGS. 1 and 2 are connected with each other via a reference character (P) and FIGS. 2 and 3 are connected with each other via a reference character (T).

When the measuring electrode 4 is inserted into the connector 3 of the apparatus 1 at step S1, the detecting circuit 52 outputs a mounting detection signal to the CPU 50. Upon receipt of the signal, the CPU 50 outputs a signal to the buzzer 59. Then, the buzzer 59 generates an alarm indicating that the measuring electrode 4 has been inserted into the connector 3. At step S2, all segments of the LCD 2 are turned on for two seconds under the control of the CPU 50. The connector 3 and the detecting circuit 52 correspond to the electrode detecting means.

At step S3, the battery checking device 58 detects the voltage of the power battery 57 incorporated in the measuring apparatus 1. At step S4, under the control of the CPU 50, electric current is applied to the electrode 45 inserted into the connector 3 via the reaction voltage setting circuit 63 and the current/voltage converter 53. In this manner, the CPU 50 detects the resistance value of the electrode 45. The CPU 50 decides whether the electrode 45 is the testing one, the calibrating one or the measuring one by detecting the resistance value of the electrode 45 through the current/voltage converter 53 and the A/D converter 54. The current/voltage converter 53 and the A/D converter 54 correspond to the signal output means. The testing electrode means an electrode having a predetermined resistance value so that a predetermined blood sugar value is displayed on the LCD 2.

If it is decided at step S4 that the electrode 45 inserted into the connector 3 is the testing electrode, the program goes to a process, shown in FIG. 4 via a reference character (Q), which will be described later, whereas if it is decided at step S4 that the electrode 45 inserted into the connector 3 is the calibrating one, the program goes to a process, shown in FIG. 5, via a reference character (R) which will be described later.

Because the measuring electrode 4 has been inserted into the connector 3, the CPU 50 decides that the electrode 45 is the electrode for measuring a blood sugar value, thus starting the execution of the blood sugar value-measuring function.

The preparatory process of functions to be executed terminates at steps S1 through S4.

Figure 9:
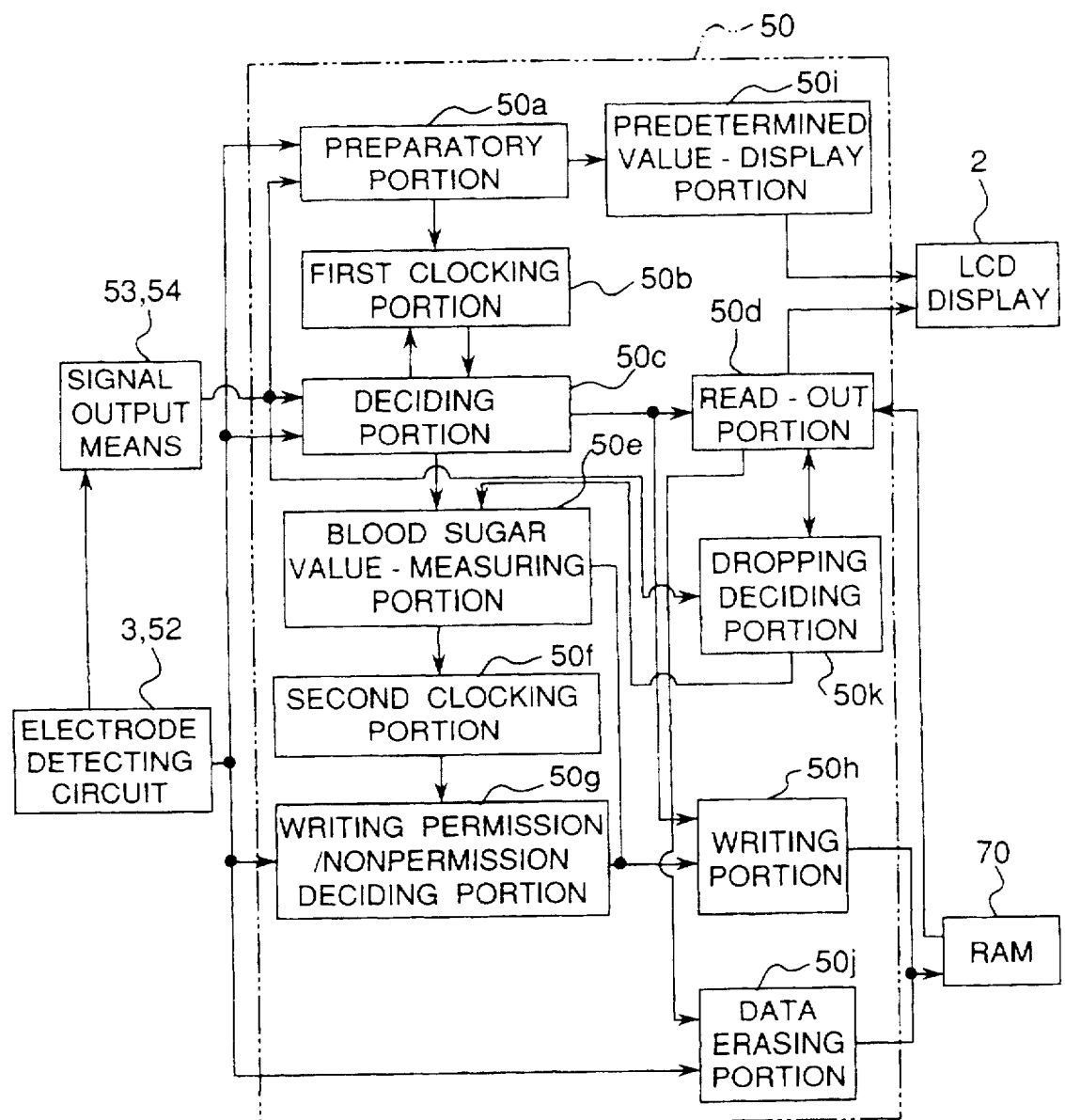
FIG. 9 is a block diagram showing the construction of a CPU shown in FIG. 8.

The operations to be executed at steps S1 through S4 correspond to the preparatory process. A preparatory portion 50a of the CPU 50 shown in FIG. 9 executes the preparatory process.

The portable measuring apparatus 1 can store 10 latest measured blood sugar values. After the preparatory process terminates at steps S1 through S4, a measurement number of the first time measurement through the 10th time measurement indicating a current measurement and a working curve number (F-0 through F-9, as shown in Table 1) indicating the kind of the working curve are alternately displayed on the LCD 2 at intervals of one second at step S5.

At step S6, the CPU 50 starts clocking one minute from the point when the preparatory process has terminated, namely, from the point when the alternate display of the measurement number and the working curve number has been started. It is to be noted that the clocking time period is not limited to one minute.

The operations to be executed at steps S5 and S6 correspond to the first clocking process. A first clocking portion 50b of the CPU 50 shown in FIG. 9 executes the first clocking process.

At step S7, the CPU 50 decides whether or not the resistance value of the measuring electrode 4 has changed rapidly due to the dropping of blood to the measuring electrode 4 during the period of time from the point when clocking operation has started until the termination of one minute. If the dropping of the blood has been detected at step S7, the program goes to step S11 which will be described later to measure the blood sugar value, whereas if the dropping of the blood has not been detected at step S7, the program returns to step S5.

The operation to be executed at step S7 corresponds to the deciding process. A deciding portion 50c of the CPU 50 shown in FIG. 9 executes the deciding process.

At steps S6 and S7, it is possible to drop control liquid to the measuring electrode 4 instead of blood. The control liquid-measuring function is described below.

The control liquid means liquid having a density adjusted to a known, or predetermined density of measuring element in the biological body fluid. In this embodiment, the measuring element is glucose, so the control liquid has a predetermined density of glucose. The control liquid-measuring function means a function of checking whether or not a measuring/calculating circuit or the like of the portable measuring apparatus 1 is abnormal and whether or not measuring electrodes having the same lot number as that of the measuring electrode 4 used to the control liquid-measuring function of the control liquid has a defect, based on the operator's decision that a blood sugar value, corresponding to the density of glucose of the control liquid, indicated on the LCD 2 by dropping the control liquid to the measuring electrode 4 is included within a predesignated blood sugar value. The blood sugar value measured by using the control liquid is stored in the RAM 70. In order to distinguish the blood sugar value, measured by using blood, to be stored in the RAM 70 and the blood sugar value, measured by using the control liquid, to be stored in the RAM 70 from each other, the following operation is performed in dropping the control liquid to the measuring electrode 4.

At steps S6 and S7, the measuring electrode 4 is pulled out from the portable measuring apparatus 1. As a result, the alternate display of the measurement number and the working curve number terminates, and either the former or the latter remains displayed on the LCD 2 for three seconds. When the measuring electrode 4 is inserted into the connector 3 again during the three seconds, as a display indicating that the control liquid is measured next, for example, the display of a character "C" and the display of characters "F-0" indicating the display of the working curve number are made alternately on the LCD 2. In this manner, the control liquid-measuring function is performed. When the measuring electrode 4 is not inserted into the connector 3 within the three seconds, the power supply is turned off. When the control liquid is dropped to the measuring electrode 4, a measuring operation is performed similarly to the method of dropping blood to the measuring electrode 4, and the RAM 70 stores the character, for example, "C" indicating the measured value of the control liquid and the blood sugar value measured by using the control liquid. The method of measuring a blood sugar value by dropping blood to the measuring electrode 4 is described later.

If it is decided at step S6 that blood has not been dropped on the measuring electrode 4 within one minute, the program goes to step S8. At step S8, the CPU 50 reads the data of measured blood sugar values stored in the RAM 70, thus outputting memory numbers and the data of the measured blood sugar values corresponding to the respective memory numbers to the LCD 2 in this order. The LCD 2 displays the memory numbers and the data of the measured blood sugar values corresponding to the respective memory numbers in this order.

The operation to be executed at step S8 corresponds to the read-out process. A read-out portion 50d of the CPU 50 shown in FIG. 9 executes the read-out process.

The display of the memory numbers and that of the data of the measured blood sugar values corresponding to the respective memory numbers are described below with reference to FIG. 6 and Tables 2-4. First, the display of a character, for example, "A" indicating the average value of all measured blood sugar values stored in the RAM 70 is displayed on the LCD 2 for one second and then, the display of the character "A" is terminated and then, the average value is displayed for two seconds. Then, as shown in Table 2, a latest measured blood sugar value through an oldest one are sequentially displayed. That is, when the two seconds have elapsed, the display of the average value is terminated and then, "3" which is the memory number storing the latest measured blood sugar value is displayed for one second. When one second has elapsed, the display of the character "3" is terminated and then, a measured blood sugar value corresponding to the memory number "3" is displayed for two seconds. At the termination of two seconds during which the measured blood sugar value corresponding to the memory number "3" is displayed, the display of the measured blood sugar value corresponding to the memory number "3" is terminated. Then, a memory number "2" is displayed for one second. When one second has elapsed, the display of the character "2" is terminated and then, a measured blood sugar value corresponding to the memory number "2" is displayed for two seconds. Similarly, the displays of measured blood sugar values corresponding to the memory numbers "5" and "4" are sequentially executed.

The read-out method of the data of the measured blood sugar values stored in the RAM 70 is not limited to the above-described one, but it is possible to display the measured blood sugar values in the order from the oldest one to the latest one and alter the above-described display time period of each data to a different one.

Table 4 shows an example the read-out of the data of measured blood sugar values from the RAM 70 when the control liquid-measuring function is executed and a blood sugar value measured by using the control liquid is stored in the RAM 70. A character "C" in Table 4 shows a portion in which the control liquid-measuring function has been executed. When the control liquid-measuring function is executed and the blood sugar value measured by using the control liquid is stored in the RAM 70, the above-described average value is calculated based on only the data of the blood sugar values measured by using blood. That is, the data of the blood sugar values measured by using the control liquid is not used in finding the average value.

TABLE 2

| memory No. | 4 | 5 | 6 | 7 | 8 | 9 | 10 | 1 | 2 | 3 |
|---|---|---|---|---|---|---|---|---|---|---|
| data | oldest | | | | →  | | | | latest | |
| read-out order | A | 3 | 2 | 1 | 10 | 9 | 8 | 7 | 6 | 5 | 4 |

TABLE 3

| memory No. | 4 | 5 | 6 | 7 | 8 | 9 | 10 | 1 | 2 | 3 |
|---|---|---|---|---|---|---|---|---|---|---|
| data | oldest | | | | → | | | | latest | |
| read-out order | A | 4 | 5 | 6 | 7 | 8 | 9 | 10 | 1 | 2 | 3 |

TABLE 4

| memory No. | 4 | 5 | 6 | C | 7 | 8 | 9 | 10 | 1 | 2 |
|---|---|---|---|---|---|---|---|---|---|---|
| data | oldest | | | | → | | | | latest | |
| read-out order | A | 2 | 1 | 10 | 9 | 8 | 7 | C | 6 | 5 | 4 |

At step S9, it is decided whether the display of all the measured blood sugar values stored in the RAM 70 has terminated. If the display of all the measured blood sugar values stored in the RAM 70 has terminated at step S9, the power supply of the measuring apparatus 1 is turned off.

If it is detected at step S10 that the blood or the control liquid has been dropped to the measuring electrode 4 before the displays of all the measured blood sugar values terminate at step S9, the program goes to step S11.

As described above, in the embodiment, the measuring apparatus 1 can display the blood sugar values stored in the RAM without providing with an operation button.

The operation to be executed at step S10 corresponds to the dropping deciding process. A dropping deciding portion 50k of the CPU 50 shown in FIG. 9 executes the dropping deciding process.

Furthermore, if the electrode is installed on or removed from the portable measuring apparatus 1 between the operation to be executed at step S8 and the operation to be executed at step S9, namely, while the data of the measured blood sugar values read out from the RAM 70 is being outputted to the LCD 2, the data of all the measured blood sugar values stored in the RAM 70 is erased.

That is, it is decided at step S50 whether the electrode is removed from the portable measuring apparatus 1. If the electrode is not removed therefrom at step S50, the program goes to step S9, whereas if the electrode is removed therefrom at step S50, the program goes to step S51.

It is decided at step S51 whether the electrode has been mounted again on the portable measuring apparatus 1 within three seconds after the electrode is removed therefrom. If the answer is "no" at step S51, the power supply is turned off. At this time, the data of the measured blood sugar values stored in the RAM 70 is not erased. If the answer is "yes" at step S51, the program goes to step S52 at which the data of all the measured blood sugar values stored in the RAM 70 is erased. Then, the power supply is turned off.

The operations to be executed at steps S50 through S52 correspond to the data erasing process. A data erasing portion 50j shown in FIG. 9 executes the data erasing process.

The period of time between the point when the electrode is removed from the connector 3 and the point when the electrode is mounted thereon again is not limited to three seconds. It is also possible to erase a part of all the data stored in the RAM 70.

Further, the kind of the electrode to be mounted on or removed from the portable measuring apparatus 1 is not limited to a specific kind of electrode.

As described above, in the embodiment, the measuring apparatus 1 can erase the data of the blood sugar values stored in the RAM 70 without providing with the operation button.

The operation of starting the measurement of a blood sugar value is described below, supposing that blood or the control liquid has been dropped to the measuring electrode 4 within one minute at steps S6 and S7 or the dropping of the blood or the control liquid has been detected at step S10.

In this case, the CPU 50 measures atmospheric temperature T1 at step S11 by using a thermistor mounted on the portable measuring apparatus 1 immediately before the blood sugar value is measured.

At steps S12 and S13, the CPU 50 waits for a predetermined reaction time period from the point when the dropping of the blood to the measuring electrode 4 has been detected at step S1 until the point when the reaction of the blood dropped to the measuring electrode 4 and a reagent layer formed in the measuring electrode 4 takes place. At step S14, when the reaction time period has terminated, the CPU 50 measures a temperature T2 by using the thermistor immediately after the blood sugar value is measured.

At step S15, the CPU 50 subtracts the temperature T1 measured at step S11 from the temperature T2 measured at step S14, thus deciding whether the absolute value of a value obtained by the subtraction is greater than a predetermined value K. If the absolute value is greater than the value K, the LCD 2 executes an error display under the control of the CPU 50. The temperature in the reaction of the blood and the reagent layer of the measuring electrode 4 affects greatly on a measured blood sugar value. Thus, when the temperature difference between the temperature before the measurement and that after the measurement is higher than the predetermined value K, the measured blood sugar value is not reliable. If the absolute value is equal or less to the value K at step S15, the program goes to step S17 at which the CPU 50 issues an instruction to the reaction voltage setting circuit 63 to apply a predetermined voltage to the measuring electrode 4, thus measuring the value of oxidation current. Based on the measured value of the oxidation current, the CPU 50 calculates a blood sugar value, thus outputting a signal to the LCD 2 at step S18 so that the blood sugar value is displayed thereon. In displaying the blood sugar value, the CPU 50 also outputs a signal to the buzzer 59 to inform a user of the completion of the measurement.

The operations to be executed at steps 12, 13, 17, and 18 are similar to those to be executed in the blood sugar value-measuring apparatus disclosed in the Patent Publication.

The operations to be executed at steps S11 through S17 correspond to the blood sugar value-measuring process. A blood sugar value-measuring portion 50e of the CPU 50 shown in FIG. 9 executes the blood sugar value-measuring process in this embodiment.

At step S19, the CPU 50 decides whether three minutes have elapsed from the start point of the display of the measured blood sugar value executed at step S18, namely, from the point when the process of measuring the blood sugar value has been completed. The operations to be executed at steps S18 and S19 correspond to the second clocking process. A second clocking portion 50f of the CPU 50 shown in FIG. 9 executes the second clocking process.

It is decided at step S20 whether or not the user has pulled out the measuring electrode 4 from the connector 3 before the three minutes elapse. This decision is made based on whether the mounting detection signal has been supplied from the detecting circuit 52 to the CPU 50. If the measuring electrode 4 is not pulled out therefrom at step S20, the program returns to step S18, thus executing operations between steps S18 and S20, whereas if the measuring electrode 4 is pulled out therefrom at step S20, the program goes to step S21. The decision as to whether the mounting detection signal has been supplied from the detecting circuit 52 to the CPU 50 is made based on the level, namely, a high level and a low level of the mounting detection signal.

At step S21, the CPU 50 starts counting three seconds from the point when the CPU 50 has detected the removal of the measuring electrode 4 from the connector 3 at step S20, thus deciding whether or not the measuring electrode 4 has been inserted into the connector 3 again within the three seconds based on whether the mounting detection signal has been supplied from the detecting circuit 52 to the CPU 50. If the CPU 50 has detected the insertion of the measuring electrode 4 within three seconds at step S21, the CPU 50 outputs a signal to the RAM 70 not to store the data of the currently measured blood sugar value, namely, to execute the measurement result-erasing function, the power supply of the measuring apparatus 1 is turned off under the control of the CPU 50. If the CPU 50 has not detected the insertion of the measuring electrode 4 within three seconds at step S21, the program goes to step S22 at which the RAM 70 stores the data of the currently measured blood sugar value. Then, the power supply is turned off.

If the measuring electrode 4 is not removal from the connector 3 at step S20, the program returns to step S18 to continue the operations at steps S18 through S20. When it is decided at step S19 that three minutes have elapsed, the program goes to step S22 at which the RAM 70 stores the data of the currently measured blood sugar value.

The operations to be executed at steps S20 and S21 correspond to the writing permission/nonpermission deciding process. A writing permission/nonpermission deciding portion 50g of the CPU 50 shown in FIG. 9 executes the writing permission/nonpermission deciding process. The operation to be executed at step S22 corresponds to the writing process. A writing portion 50h of the CPU 50 shown in FIG. 9 executes the writing process.

Figure 4:
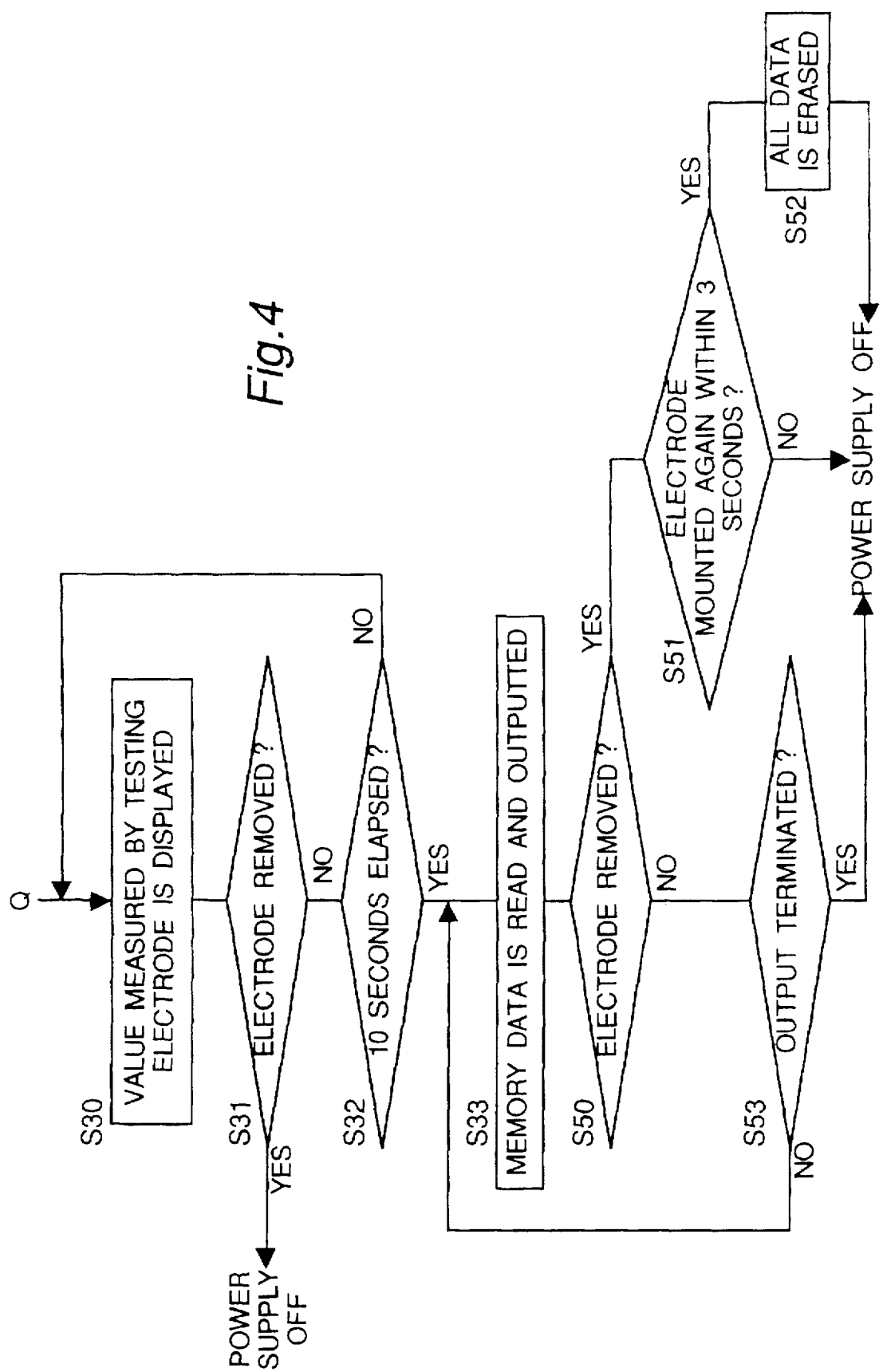
FIG. 4 is a flowchart showing an embodiment of the operation of a measuring function to be executed by means of a testing electrode.
Figure 5:
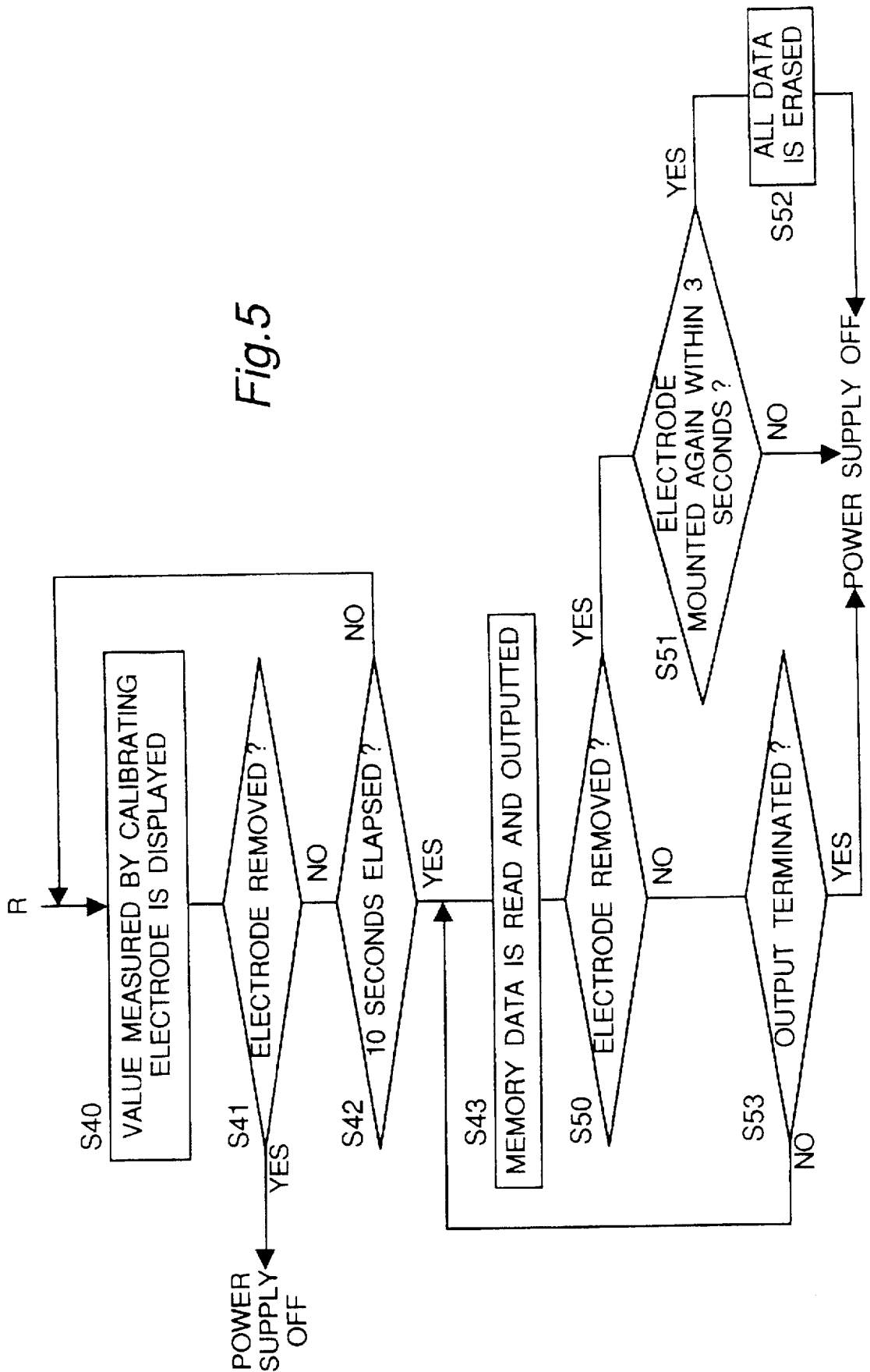
FIG. 5 is a flowchart showing an embodiment of the operation of a correcting function.

Description is made on an embodiment of the data managing method in performing a measuring function by means of the testing electrode and the calibrating (switch-over of working curve) function with reference to FIGS. 4 and 5, supposing that the testing electrode or the calibrating electrode has been inserted into the connector 3.

The measuring function by means of the testing electrode means a function to check whether or not the portable measuring apparatus 1 operates normally. The CPU 50 decides that the electrode inserted into the connector 3 is the testing electrode according to a predetermined resistance value of the testing electrode and converts the resistance value into a blood sugar value in case of this embodiment, thus outputting a signal to the LCD 2 so that the measured blood sugar value is displayed thereon.

Referring to FIG. 4, the operation of the measuring function by means of the testing electrode is described below. When it is decided at step S4 that the electrode inserted into the connector 3 is the testing electrode, the program goes to step S30 at which the CPU 50 converts the resistance value of the testing electrode into a blood sugar value, thus outputting a signal to the LCD 2 so that the measured blood sugar value measured by means of the testing electrode is displayed thereon.

It is decided at step S31 whether or not the testing electrode has been pulled out from the connector 3. The CPU 50 makes the decision based on whether or not the detecting circuit 52 has supplied the mounting detection signal to the CPU 50. If the testing electrode has been pulled out therefrom at step S31, the power supply of the portable measuring apparatus 1 is turned off under the control of the CPU 50. If the testing electrode has not been pulled out therefrom at step S31, the CPU 50 decides at step S32 whether or not 10 seconds have elapsed from the point when the electrode was inserted into the connector 3 at step S1. If 10 seconds have not elapsed and the testing electrode has not been pulled out from the connector 3, the program returns to step S30 to repeatedly perform the operations at steps S30 through S32. When 10 seconds have elapsed at step S32 without the testing electrode being removed from the connector 3, the program goes to step S33 at which the CPU 50 reads out the data of the past 10 measured blood sugar values stored in the RAM 70, thus outputting the data of the 10 measured blood sugar values sequentially to the LCD 2. The data of the 10 measured blood sugar values is displayed in the same procedure as that to be performed at step S8.

It is probable that the CPU 50 performs the data erasing operation (step S50 through S52) as described above before the output of the data of all the measured blood sugar values read out from the RAM 70 is completed. That is, it is decided at step S50 subsequent to step S33 whether or not the electrode has been removed from the portable measuring apparatus 1. If the electrode has not been removed therefrom at step S50, the program goes to step S53, whereas if the electrode has been removed therefrom at step S50, the program goes to step S51.

It is decided at step S51 whether or not the electrode has been mounted again on the portable measuring apparatus 1 within three seconds after the removal of the electrode therefrom. If the electrode has not been mounted again at step S51, the power supply is turned off under the control of the CPU 50. At this time, the data of the measured blood sugar values stored in the RAM 70 is not erased. If the electrode has been mounted again at step S51, the program goes to step S52 at which the CPU 50 erases the data of all the measured blood sugar values stored in the RAM 70. Then, the power supply is turned off under the control of the CPU 50.

It is decided at step S53 whether the output of the data of all the measured blood sugar values read out from the RAM 70 is completed. If the output is not completed at step S53, the program returns to step S33, whereas if the output is completed at step 53, the power supply is turned off.

The calibrating (switch-over of working curve) function means a function to specify one working curve from among data of a plurality of working curve stored in the portable measuring apparatus 1. The CPU 50 decides that an electrode inserted into the connector 3 is the calibrating electrode according to a predetermined resistance value of the electrode, thus specifying a working curve designated by the calibrating electrode.

The operation of the calibrating function is described below with reference to FIG. 5. If it is decided at step S4 that an electrode inserted into the connector 3 is the calibrating electrode, the program goes to step S40 at which the working curve number is displayed on the LCD 2 under the control of the CPU 50, based on the resistance value of the calibrating electrode.

It is decided at step S41 whether or not the calibrating electrode has been pulled out from the connector 3. The CPU 50 makes the decision based on whether or not the detecting circuit 52 has outputted the mounting detection signal to the CPU 50. If the calibrating electrode has been pulled out from the connection 3 at step S41, the power supply of the portable measuring apparatus 1 is turned off under the control of the CPU 50. If the calibrating electrode has not been pulled out from the connection 3 at step S41, the CPU 50 decides whether or not 10 seconds have elapsed from the point when the electrode was inserted into the connector 3 at step S1. If 10 seconds have not elapsed and the calibrating electrode has not been pulled out from the connector 3, the program returns to step S40 to repeatedly perform the operations at steps S40 through S42. When 10 seconds have elapsed at step S42 without the calibrating electrode being removed from the connector 3, the program goes to step S43 at which the CPU 50 reads out the data of the past 10 measured blood sugar values stored in the RAM 70, thus outputting the data of the read-out measured blood sugar values sequentially to the LCD 2. The data of the read-out measured blood sugar values is displayed in the same procedure as that to be performed at step S8.

It is probable that the CPU 50 executes the data erasing operation (step S50 through S52) as described above before the output of the data of all the measured blood sugar values read out from the RAM 70 is completed. That is, it is decided at step S50 subsequent to step S43 whether or not the electrode has been removed from the portable measuring apparatus 1. If the electrode has not been removed therefrom at step S50, the program goes to step S53, whereas if the electrode has been removed therefrom at step S50, the program goes to step S51.

It is decided at step S51 whether or not the electrode has been mounted again on the portable measuring apparatus 1 within three seconds after the removal of the electrode therefrom. If the electrode has not been mounted again at step S51, the power supply is turned off under the control of the CPU 50. At this time, the data of the measured blood sugar values stored in the RAM 70 is not erased. If the electrode has been mounted again at step S51, the program goes to step S52 at which the CPU 50 erases the data of all the measured blood sugar values stored in the RAM 70. Then, the power supply is turned off.

It is decided at step S53 whether the output of the data of all the measured blood sugar values read out from the RAM 70 is completed. If the output is not completed at step S53, the program returns to step S43, whereas if the output is completed at step 53, the power supply is turned off.

As described above, the data stored in the RAM 70 can be displayed as short as 10 seconds after the testing electrode or the calibrating electrode is inserted into the connector 3, whereas the data stored in the RAM 70 is displayed as long as one minute after the measuring electrode 4 is inserted into the connector 3.

The operations to be executed at steps S30 and S40 correspond to the predetermined value-display process. A predetermined value-display portion 50$i$ of the CPU 50 shown in FIG. 9 executes the predetermined value display process. The operations to be executed at steps S31 through S33 and S41 correspond to the first clocking process, the deciding process, and the read-out process, respectively.

In the above embodiment, the portable measuring apparatus 1 has no operation button, so, the operations, e.g. the operation for reading out the measured blood sugar value. the operation for erasing the measured blood sugar value and so on, are executed by mounting the electrode on the portable measuring apparatus 1 and removing the electrode therefrom.

However, the portable measuring apparatus may have at least one operation button, and thus at least one of the operations may be executed by the operation button.

As described above, according to the article of manufacture comprising a computer usable medium of the present invention, as the computer usable medium embodies computer-readable program code detecting means, computer-readable program code characteristic measuring means, computer-readable program code clocking means, computer-readable program code determining means, computer-readable program code density measuring means, computer-readable program code density storing means, computer-readable program code read out means, and computer-readable program code output means, the measuring apparatus comprising the article of manufacture can smoothly measure the density data, store the measured density data to the storing means, and read out the measured density data from the storing means.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. An article of manufacture comprising:
   a computer usable medium, including computer-readable program code means embodied therein, for causing a computer to manage data in a measuring apparatus, the computer-readable program code means in the article of manufacture comprising:
   computer-readable program code detecting means for causing the computer to detect whether an electrode has been mounted on the measuring apparatus;
   computer-readable program code characteristic measuring means for causing the computer to measure a characteristic of the electrode to determine what type of electrode has been mounted on the measuring apparatus;
   computer-readable program code clocking means for causing the computer to clock a first period of time after the computer has measured the characteristic of the electrode;
   computer-readable program code determining means for causing the computer to determine whether an execution for clocking the first period of time has been switched over to an execution for measuring density of an element included in a biological body fluid before a termination point of the first period of time;
   computer-readable program code density measuring means for causing the computer to measure density of the element included in the biological body fluid which has been placed on the electrode when the execution for the first period of time has been switched over to the execution for measuring density of the element included in the biological body fluid before a termination point of the first period of time;
   computer-readable program code density storing means for causing the computer to store a measured density of the element included in the biological body fluid in a storing means; and computer-readable program code read out and output means for causing the computer to read out measured density data stored in the storing means
   and then output the measured density data read out from the storing means when the first period of time has reached a termination point without being switched over to the execution for measuring density of the element included in the biological body fluid.

2. The article of manufacture as claimed in claim 1, wherein the program code means further comprises:
   computer-readable program code erasing means for causing the computer to determine whether to erase the measured density data in the storing means when the mounted electrode has been removed from the measuring apparatus before all of the measured density data read out from the storing means is outputted and then the electrode has been mounted thereon.

3. The article of manufacture as claimed in claim 1, wherein the program code means further comprises:
   computer-readable program code writing permission/ nonpermission determining means for causing the computer to determine whether to store the measured density data to the storing means.

4. The article of manufacture as claimed in claim 2, wherein the program code means further comprises:
   computer-readable program code writing permission/ nonpermission determining means for causing the computer to determine whether to store the measured density data to the storing means.

5. The article of manufacture as claimed in claim 1, wherein the program code means further comprises:
   computer-readable program code value displaying means for causing the computer to display a value based on a resistance value of an electrode mounted on the measuring apparatus when a resistance value measuring electrode has been mounted on the measuring apparatus.

6. The article of manufacture as claimed in claim 4, wherein the program code means further comprises:
   computer-readable program code value displaying means for causing the computer to display a value based on a resistance value of an electrode mounted on the measuring apparatus when a resistance value measuring electrode has been mounted on the measuring apparatus.

7. The article of manufacture as claimed in claim 1, wherein the biological body fluid is blood, the element of the biological body fluid is glucose, and the density data of the element is a blood sugar value.

8. The article of manufacture as claimed in claim 4, wherein the biological body fluid is blood, the element of the biological body fluid is glucose, and the density data of the element is a blood sugar value.

9. The article of manufacture as claimed in claim 1, wherein the biological body fluid is blood plasma.

10. The article of manufacture as claimed in claim 1, wherein the biological body fluid is blood serum.

11. The article of manufacture as claimed in claim 1, wherein the biological body fluid is urine.

12. The article of manufacture as claimed in claim 1, wherein the element is lactic acid.

13. The article of manufacture as claimed in claim 1, wherein the element is cholesterol.

14. The article of manufacture as claimed in claim 1, wherein the element is uric acid.

15. The article of manufacture as claimed in claim 1, wherein the element is triglyceride.

* * * * *